United States Patent [19]

Janah et al.

[11] Patent Number: 5,650,620

[45] Date of Patent: Jul. 22, 1997

[54] METHOD AND DEVICE FOR VERIFYING THAT A GIVEN INSULATIVE ELEMENT CONFORMS TO A REFERENCE INSULATIVE ELEMENT

[75] Inventors: Hakim Janah, Sangatte; Daniel Acroute, March; Pierre Mirebeau, Villebon sur Yvette; Claude Le Gressus; Claude Faure, both of Paris, all of France

[73] Assignees: Alcatel Cable, Clichy; Commissariat a l'Energie Atomique, Paris, both of France

[21] Appl. No.: 623,149

[22] Filed: Mar. 28, 1996

[30] Foreign Application Priority Data

Mar. 30, 1995 [FR] France .................................. 95 03771

[51] Int. Cl.$^6$ .................................................. H01J 37/256
[52] U.S. Cl. ........................ 250/310; 324/751; 324/71.1
[58] Field of Search ................................ 250/310, 306, 250/307, 397, 398, 399, 400, 492.1, 492.2, 492.3; 324/751, 558, 71.1, 96, 158.1

[56] References Cited

U.S. PATENT DOCUMENTS 4,745,362  5/1988  Brust ........................................ 250/310
5,281,909  1/1994  Brust ........................................ 250/310

FOREIGN PATENT DOCUMENTS

| 0114765A3 | 8/1984 | European Pat. Off. . |
| 0122653A1 | 10/1984 | European Pat. Off. . |
| 0129508A1 | 12/1984 | European Pat. Off. . |
| 0342354A2 | 11/1989 | European Pat. Off. . |
| 0497397A1 | 8/1992 | European Pat. Off. . |

*Primary Examiner*—Jack I. Berman
*Assistant Examiner*—Kiet T. Nguyen
*Attorney, Agent, or Firm*—Sughrue, Mion, Zinn, Macpeak & Seas

[57] ABSTRACT

A method of verifying that a given insulative element conforms with a reference insulative element, comprising the steps of: emitting a primary beam of electrons impinging on the given insulative element, receiving a secondary beam of electrons returned by the given insulative element in response to emission of the primary beam of electrons, and comparing a curve as a function of time of the electrical current of the secondary beam received with a curve as a function of time of a reference electrical current to establish whether or not the given insulative element conforms to a reference insulative element.

8 Claims, 2 Drawing Sheets

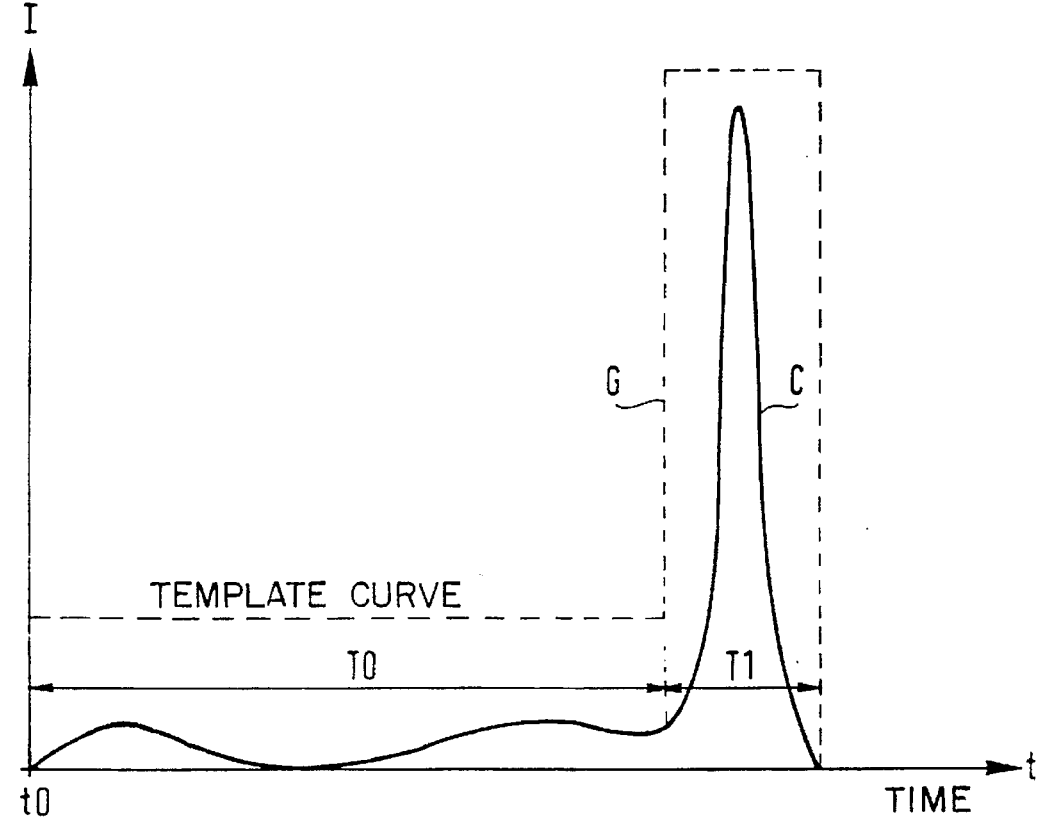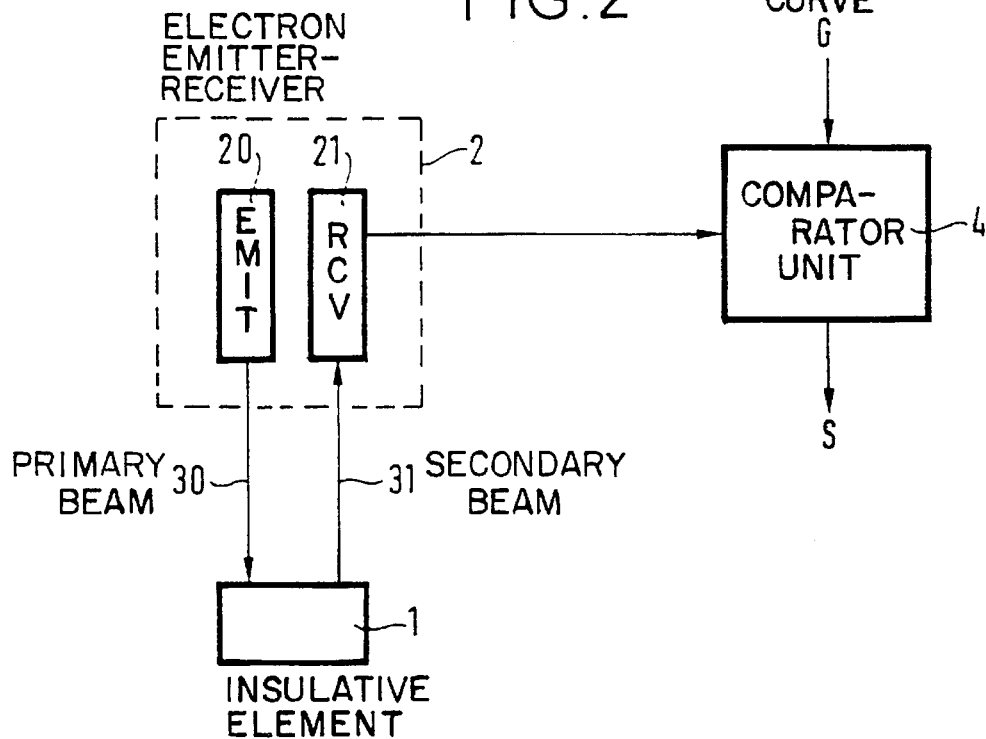

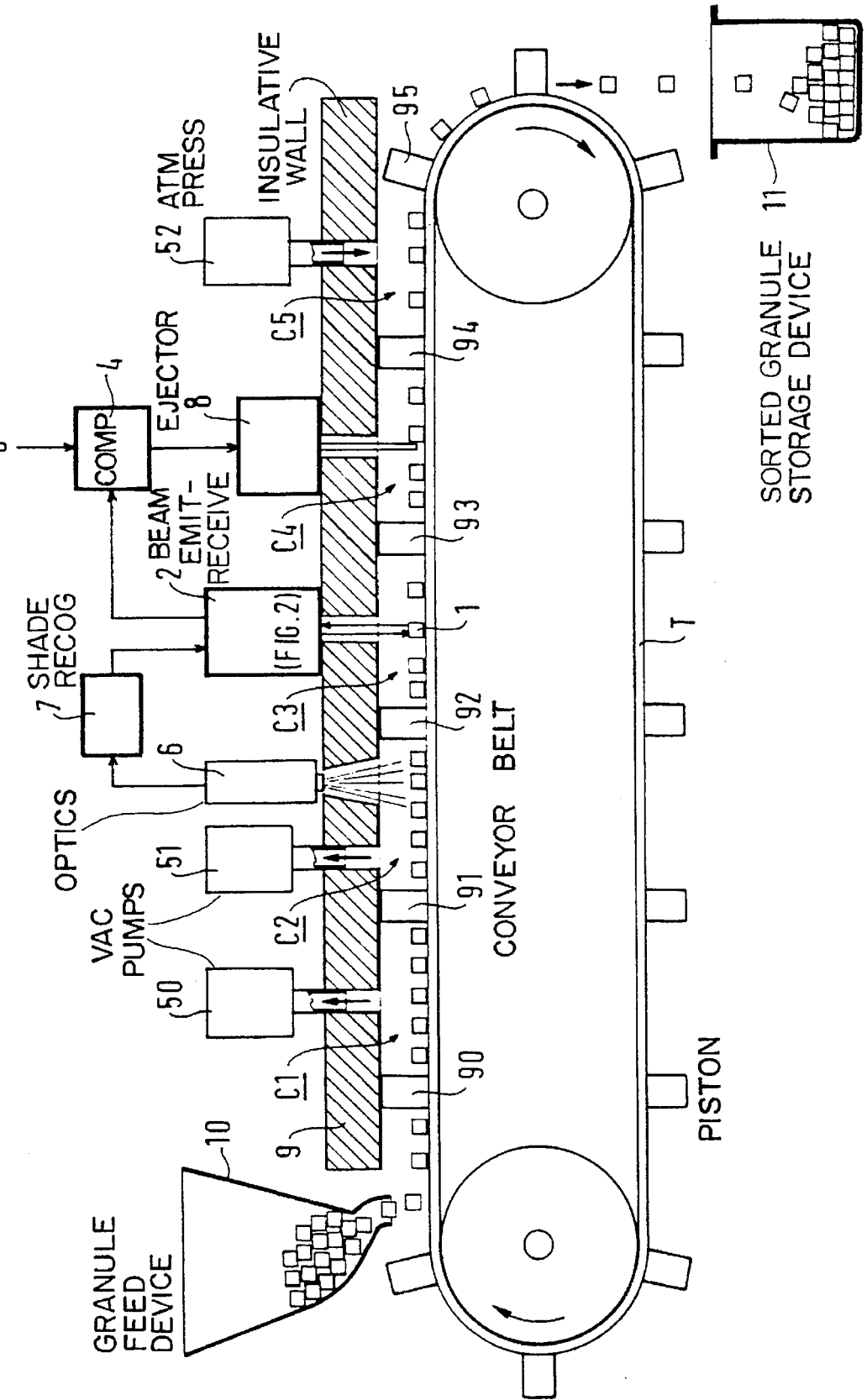

METHOD AND DEVICE FOR VERIFYING THAT A GIVEN INSULATIVE ELEMENT CONFORMS TO A REFERENCE INSULATIVE ELEMENT

BACKGROUND OF THE INVENTION

1. Field of the Invention

The present invention is generally concerned with insulative materials and more particularly with devices and methods for verifying that such materials conform to a reference material in order to detect defects or contamination of such materials. The invention further concerns a method for sorting insulative material granules to be used to manufacture power cable sheathing, for example.

2. Description of the Prior Art

Detecting defects and/or contamination of insulative materials is of primary importance in the case of synthetic insulative materials that are used to manufacture sheathing of high or very high voltage power cables, for example. The very high voltages at which these cables operate require very extensive quality control to guarantee the quality of the insulative materials used to manufacture the insulative sheathing of the cable. The smallest defect in the insulative sheathing can lead to breakdown of the insulative material and thus to irreversible deterioration of the cable.

The synthetic insulative material to be used to manufacture insulative cable sheathing is in practise shipped in the form of insulative material granules, each having a very small volume, in the order of ten cubic millimeters. The granules are heated for an extrusion operation. Various kinds of defects and/or contamination affect the granules. They comprise surface contamination, volume contamination and generalized volume defects.

Surface contamination is caused by cutting up the insulative material to produce the granules and transporting the resulting granules. It comprises mechanical fines, polymer dust, mineral contaminants and exudation from the constituents. The mechanical fines are the result of the cutting operation, which produces insulative material dust which is deposited onto the granules formed by the cutting operation. The mineral contaminants are caused by contact of the granules with external elements, such as metal or plastics material transportation containers, which cause localized deposition of plastics material or metal micro-elements on the granules.

The volume contamination is the result of the operation by which the insulative material is manufactured. It comprises conductive or insulative mineral bodies that are locally integrated into the volume of a granule. These mineral bodies are present in the furnace in which the insulator is made, for example, in the additives required to manufacture it or in the manufacturing environment. An oxidized area can also appear following prolonged contact with oxygen at a high temperature.

The volume defects are in the form of generalized defects in the chemical structure of the granule. They originate in malfunctions of the reactor in which the insulator is manufactured, for example.

Contamination and defects of the above kind in practise affect only a relatively small percentage of the granules. However, it is essential to provide a method of detecting such imperfections wherever possible and for rejecting imperfect granules if the imperfection cannot be eliminated.

Various prior art techniques are available for eliminating surface contamination on the granules. They include washing in a solvent such as methanol, for example. Eliminating surface contamination does not pose any particular problem, and the prior art provides well proven techniques for this.

Eliminating volume contamination and defects relies on optical techniques that are not entirely satisfactory. The objective of such techniques is to reject granules that have volume contamination and/or defects, given that volume imperfections of the granules cannot be corrected. Broadly speaking, they involve projecting a light beam onto each granule in order to obtain an image of each granule. Image processing is then used to detect a color difference between the color of at least a localized area of the granule of interest and a reference color. The color difference determines whether the granule has any imperfection and must therefore be rejected. This optical technique has the drawback of being relatively inefficient in the case of volume contamination and even less efficient in the case of generalized volume defects. Being based on detecting granule imperfections by chromatic analysis, the technique is inherently limited by the fact that volume contamination or defects do not necessarily cause any chromatic differentiation, or at least any differentiation detectable by optical means.

A first objective of the invention is to provide a method and device for verifying that a given insulative element conforms to a reference insulative element, in order to detect efficiently volume defects and contamination of the given insulative element, e.g. granule.

A second objective of the invention is to provide a method of sorting insulative material granules.

A final objective of the invention is to provide a power cable manufactured from insulative material granules sorted by the above method.

SUMMARY OF THE INVENTION

To this end, a method in accordance with the invention of verifying that a given insulative element conforms with a reference insulative element, comprises the steps of:

emitting a primary beam of electrons impinging on said given insulative element, receiving a secondary beam of electrons returned by said given insulative element in response to emission of said primary beam of electrons, and comparing a curve as a function of time of the electrical current of said secondary beam received with a curve as a function of time of a reference electrical current to establish whether or not said given insulative element conforms to a reference insulative element.

A device for implementing the above method comprises:

means in accordance with the invention for emitting a primary beam of electrons impinging on said given insulative element, means for receiving a secondary beam of electrons returned by said given insulative element in response to emission of said primary beam of electrons, and means for comparing a curve as a function of time of the electrical current of said secondary beam received and a curve as a function of time of a reference electrical current held in memory.

A method in accordance with the invention of sorting insulative material granules comprises the steps of:

emitting a primary beam of electrons impinging on each of said granules, receiving a secondary beam of electrons returned by each of said granules in response to emission of said primary beam of electrons, comparing a curve as a function of time of the electrical current of said secondary beam received with a curve as a function of time of a reference electrical current associated with a reference granule, and ejecting granules selectively in accordance with a negative result of comparing said curve as a function of time of the electrical current of said secondary beam received and said curve as a function of time of said reference electrical current associated with said reference granule.

The curve as a function of time of said reference electrical current is preferably a template curve established from a curve as a function of time of the electrical current of a secondary beam of electrons returned by said reference granule in response to emission of a primary beam of electrons impinging on said reference granule and said comparison step consists in verifying that said curve as a function of time of the electrical current of said secondary beam received is inscribed in said template curve.

The primary beam of electrons advantageously has an electrical current as a function of time identical, ignoring a proportionality factor, to an electrical voltage as a function of time to be simulated on said granule.

The step of emitting a primary beam of electrons impinging on said granules is preceded by a step of evacuating a chamber containing said granules in order to achieve perfect propagation of the primary beam of electrons.

The granules to be sorted typically move continuously and said emission of a primary beam of electrons impinging on each of said granules is activated in response to detection by shape recognition means of the passage of each of said granules.

The granules are advantageously washed beforehand in order to remove surface contamination.

A power cable manufactured from granules sorted by the method of the invention is of significantly better quality.

Other features and advantages of the present invention will emerge more clearly from a reading of the following description given with reference to the corresponding appended drawings.

BRIEF DESCRIPTION OF THE DRAWINGS

FIG. 1 is a graph as a function of time of the electrical current of a secondary beam of electrons returned by a reference insulative element in response to a primary beam of electrons impinging on said insulative element.

FIG. 2 is a block schematic of a device in accordance with the invention for verifying that a given insulative element conforms to a reference insulative element.

FIG. 3 shows a system in accordance with the invention for sorting insulative material granules.

DETAILED DESCRIPTION OF THE PREFERRED EMBODIMENT

Referring to FIG. 1, the invention is based on a remarkable property of the curve as a function of time of the electrical current C of a secondary beam of electrons returned by a reference insulative element in response to a primary beam of electrons impinging on that insulative element. The reference insulative element is an insulative material element selected for its purity or quality in the sense that it is free of surface or volume contamination or defects. It is bombarded by a primary beam of electrons defined by a predetermined current as a function of time. It is to be noted that this function must be a specific function, in particular in terms of current, to obtain the highly specific type of curve C shown in FIG. 1. Emission of the primary beam of electrons impinging on the insulative element starts at a time t0 and continues for a time (T0+T1). During the time T0 from time t0, the electrical current I of the secondary electron beam returned by the insulative element is virtually zero. Then, during a time T1 following on from time T0, the electrical current of the secondary beam of electrons returned by the insulative element suddenly assumes a very high value before returning to a virtually zero level. It is therefore as if the insulative element accumulates electrical charge for a given time T0 and then suddenly discharges the accumulated electrical charge during a time T1. This curve as a function of time of the electrical current C of a secondary beam of electrons returned by an insulative element is characteristic of the fact that the insulative element is free of imperfections. The inventors have experimented with two embodiments of the invention, one using a focused mode and the other a non-focused mode, both of which proved entirely satisfactory. In the focused mode the primary beam of electrons bombards a highly localized area of the insulative element at a power of 30 keV and a primary electron beam current of 500 pA for (T0+T1)=1 second. In the non-focused mode the primary beam of electrons bombards a greater area of the surface of the insulative element at a power of 30 keV and a primary electron beam current of 250 pA for (T0+T1)=10 seconds. These experimental values can of course be modified by trial and error, in particular to reduce the time (T0+T1) by increasing the current of the primary beam of electrons. Moreover, the current of the primary beam of electrons need not be constant throughout the time (T0+T1); it can be a linear function of time, for example. The above experimental values were obtained for low-density polyethylene. The validity of those values for other types of material must be verified experimentally. It should be noted that although the expression "secondary beam of electrons" is used herein, the electrons returned by the insulative element are not in the form of a concentrated ray but have a somewhat anarchic spatial distribution. A curve of this type is not obtained if the insulative element has volume contamination or defects. A template curve G constituting a coarse envelope of the curve C can be deduced from said curve C. To verify if volume contamination or defects are to be attributed to a given insulative element, the invention proposes to verify if the given insulative element conforms to a reference insulative element. To this end, it is proposed to emit a primary beam of electrons that impinges on the given insulative element and then to receive a secondary beam of electrons that is returned by the given insulative element in response to such emission. The curve of the electrical current of the secondary beam received as a function of time is then compared with a reference curve of electrical current as a function of time, obtained as described above, to establish whether the given insulative element conforms to the reference insulative element or not. The reference curve of current as a function of time is a template curve G of the type shown in FIG. 1, for example, established from a curve as a function of time of the electrical current of a secondary beam of electrons returned by the reference insulative element in response to the emission of a primary beam of electrons impinging on that insulative element. Comparison of the curve of the received electrical current as a function of time and the reference curve then consists in verifying whether said curve of the electrical current of said received secondary beam as a function of time is inscribed within said template curve, for example. If it is, it can be deduced that the insulative element is not contaminated; if it does not, it must be concluded that the insulative element is contaminated.

FIG. 2 is a block schematic showing a device for verifying that a given insulative element 1 conforms with a reference insulative element. The device comprises an electron emission/reception system 2 and a comparator unit 4. The system 2 comprises a unit 20 for emitting a primary beam of electron beams 30 and a unit 21 for receiving a secondary beam of electrons 31. The primary beam of electrons 30 impinges on the insulative element 1 to be characterized. In response to it, a secondary beam of electrons 31 is returned by the insulative element 1 and received by the unit 21. A curve as a function of time of the electric current of the secondary beam received can be obtained from the secondary beam of electrons. This curve as a function of time of the electrical current of the secondary beam received is compared in the unit 4 with a reference curve G as a function of time of electrical current stored in memory to establish whether the given insulative element 1 conforms or not with the reference insulative element.

As already mentioned, the reference curve of the electrical current as a function of time is a template curve G of the type shown in FIG. 1, for example, established from a curve as a function of time of the electrical current of a secondary beam of electrons returned by the reference insulative element in response to a primary beam of electrons impinging on the insulative element. Comparing the curve of the received electrical current as a function of time and the reference curve then consists in verifying if the curve of the electrical current C of the received secondary beam as a function of time is inscribed within the template curve G. If it is, it can be deduced that the insulative element is not contaminated; if it is not, it must be concluded that the insulative element is contaminated. Comparison by verification of inscription as effected in the unit 4 consists in practise of comparing respective samples of current I regularly taken from the curve obtained and the reference curve G. To be more precise, the unit 4 verifies if each electrical current level of the curve obtained is below a corresponding current level of the template curve G. The respective levels of the curve obtained and the template curve G are compared for the same time offset relative to a reference time t0 (FIG. 1) at which emission of the primary beam of electrons starts.

A system for sorting insulative material granules intended in particular for the manufacture of power cable sheathing will now be described with reference to FIG. 3.

The system includes a conveyor belt T on which are mounted at regular intervals pistons 90, 91, 92, 93, 94 and 95 moving transversely to the surface of the conveyor belt, an insulative wall 9, a granule feed device 10, two vacuum pumps 50 and 51, an optical unit 6, a shape recognition unit 7, an electron beam emission/reception system 2, a comparator unit 4, a granule ejector device 8, an atmospheric pressure establishing device 52 and a sorted granule storage device 11. The conveyor belt T runs at a constant speed and defines a moving horizontal worksurface having a main portion facing the fixed insulative wall 9. A perfect lateral seal between the fixed insulative wall 9 and the work surface of the conveyor belt is provided by lateral sealing devices (not seen in the longitudinal section shown). A transverse seal provided by the pistons 90–95 contacting the bottom surface of the insulative wall 9, combined with the lateral seal already mentioned, defines hermetically sealed chambers C1, C2, C3, C4 and C5. Each of the hermetically sealed chambers is delimited by the surface of the conveyor belt, the bottom surface of the insulative wall 9, the lateral sealing devices and two pistons. The chamber C1 in FIG. 3 is delimited transversely by the two pistons 90 and 91, the chamber C2 by the pistons 91 and 92, the chamber C3 by the pistons 92 and 93, and so on, the chamber C5 being defined by the two pistons 94 and 95. As the conveyor belt moves along, the successive chambers undergo the following successive operations in turn:

a1)—first application of vacuum, a2)—second application of vacuum and optical detection of the granules that it contains, a3)—verification of granule conformity by electron beam, and a4)—ejection of non-conforming granules.

The successive operations will now be described in more detail. A portion complementary to the main portion of the horizontal worksurface does not face the insulative wall 9 and, as the conveyor belt moves along, receives from the feed device 10 insulative material granules to be sorted. These granules may have been washed beforehand in order to remove surface contamination. They are ultrasonically cleaned in a liquid medium, for example. Each granule washed in this way is tipped onto the conveyor belt and, as a result of the movement of the conveyor belt, is enclosed in an hermetically sealed chamber moving relative to the insulative wall 9. It is then subjected to the above operations a1) through a4) in succession. Each granule tipped onto the conveyor belt is enclosed in an hermetically sealed chamber as the result of the two pistons delimiting the chamber being in contact with the bottom surface of the insulative wall 9 as the conveyor belt moves along. The hermetically sealed chamber is first evacuated to a given first pressure by the vacuum pump 50. The vacuum pump 50 is connected to an opening formed in the insulative wall 9. On further movement of the conveyor belt, the hermetically sealed chamber is then evacuated to a second pressure lower than said first pressure. Two vacuum operations are used in this embodiment but they can be combined into a single operation.

An optical device 6 then produces an image of the contents of the chamber and in particular of the granules contained in it and that follow a particular path in the chamber, for example in a channel. The optical device is hermetically sealed to the top surface of the insulative wall 9, a viewing hole being provided in the wall 9. The image produced by the optical device 6 is transmitted to the shape recognition unit 7. The function of the recognition unit is to detect the passage of a granule in the field of view of the optical device 6. As soon as a granule is detected, the shape recognition unit 7 actives the electron beam emission/reception system 2, which is of the type shown in FIG. 2, downstream of it in the direction in which the granules move along the conveyor belt. In response to such activation of the system 2, and by virtue of fine adjustment of the synchronization, the unit 20 (FIG. 2) emits a primary beam of electrons at a time t0 that coincides with the time at which the granule of interest, detected by the unit 7, is in the field of said primary beam of electrons emitted by the unit 20. Acquisition by the unit 21 (FIG. 2) of the curve as a function of time of the electrical current of the secondary beam returned by the granules in response to the emission of the primary beam of electrons is initialized at the same time t0. For this operation the chamber in which the granule is located is still under vacuum, because it is hermetically sealed, the system 2 being hermetically sealed to the top surface of the insulative wall 9 and the primary and secondary beams passing through an opening formed in the insulative wall 9. The curve as a function of time of the electrical current of the secondary beam that is acquired during the time (T0+T1) is transmitted in numerical form to the comparator unit 4. The function of the unit 4 is to compare the curve of the electrical current of the secondary beam received as a function of time and a reference curve G of electrical current as a function of time held in memory to establish whether the granule of interest conforms or not to a reference granule. If it does not, the granule is ejected by the ejector device 8 into an imperfect granule receiving tank (not shown) that is under vacuum. As previously described, the comparison step consists in verifying that the curve of the electrical current of the secondary beam received as a function of time is inscribed within a template curve G (FIG. 2). To verify conformity, each electric current level of the received secondary beam is verified to determine if it is below a corresponding current level of the template curve G. The respective levels of the received secondary beam and the template curve G are compared for the same time offset relative to a reference time t0 (FIG. 1) at which emission of the primary beam of electrons starts. On further movement of the conveyor belt, the chamber is returned to atmospheric pressure by the device 52. At the far end of the conveyor belt the remaining granules, i.e. those that have not been ejected, are tipped into the sorted granule storage device 11. The sorted granules do not have any volume contamination or defects. They are therefore particularly suitable for the manufacture of power cable, in particular high or very high voltage cable.

The electrical current of the primary beam of electrons as a function of time is advantageously chosen to be identical, ignoring a factor of proportionality, to an electrical voltage as a function of time to be simulated on the granule.

There is claimed:

1. Method of verifying that a given insulative element conforms with a reference insulative element, comprising the steps of:

emitting a primary beam of electrons impinging on said given insulative element, receiving a secondary beam of electrons returned by said given insulative element in response to emission of said primary beam of electrons, and comparing a curve as a function of time of the electrical current of said secondary beam received with a curve as a function of time of a reference electrical current to establish whether or not said given insulative element conforms to a reference insulative element.

2. Device for implementing the method according to claim 1, comprising:

means for emitting a primary beam of electrons impinging on said given insulative element, means for receiving a secondary beam of electrons returned by said given insulative element in response to emission of said primary beam of electrons, and means for comparing a curve as a function of time of the electrical current of said secondary beam received and a curve as a function of time of a reference electrical current held in memory.

3. Method of sorting insulative material granules, comprising the steps of:

emitting a primary beam of electrons impinging on each of said granules, receiving a secondary beam of electrons returned by each of said granules in response to emission of said primary beam of electrons, comparing a curve as a function of time of the electrical current of said secondary beam received with a curve as a function of time of a reference electrical current associated with a reference granule, and ejecting granules selectively in accordance with a negative result of comparing said curve as a function of time of said electrical current of said secondary beam received and said curve as a function of time of said reference electrical current associated with said reference granule.

4. Method according to claim 3 wherein said curve as a function of time of said reference electrical current is a template curve established from a curve as a function of time of said electrical current of said secondary beam of electrons returned by said reference granule in response to emission of said primary beam of electrons impinging on said reference granule and wherein said comparison step consists in verifying that said curve as a function of time of said electrical current of said secondary beam received is inscribed in said template curve.

5. Method according to claim 3 wherein said primary beam of electrons has an electrical current as a function of time identical, ignoring a proportionality factor, to an electrical voltage as a function of time to be simulated on said granule.

6. Method according to claim 3 wherein said step of emitting a primary beam of electrons impinging on said granules is preceded by a step of evacuating a chamber containing said granules.

7. Method according to claim 3 wherein said granules to be sorted move continuously and said emission of a primary beam of electrons impinging on each of said granules is activated in response to detection by shape recognition means of the passage of each of said granules.

8. Method according to claim 3 wherein said granules are washed beforehand in order to remove surface contamination.

\* \* \* \* \*